United States Patent [19]

Fravel, Jr. et al.

[11] Patent Number: 4,539,416
[45] Date of Patent: Sep. 3, 1985

[54] PROCESSES FOR MAKING THIOALKYL CARBOXAMIDES AND AMINES

[75] Inventors: Harold G. Fravel, Jr.; Michael J. Fazio, both of Midland, Mich.

[73] Assignee: The Dow Chemical Company, Midland, Mich.

[21] Appl. No.: 503,389

[22] Filed: Jun. 10, 1983

[51] Int. Cl.$^3$ .................. C07D 307/52; C07D 307/54
[52] U.S. Cl. ..................... 549/496; 544/152; 544/379; 546/214; 548/517; 549/492; 549/494; 549/495
[58] Field of Search ............... 549/492, 494, 495, 496; 544/152, 379; 546/214; 548/517

[56] References Cited

U.S. PATENT DOCUMENTS 4,086,273  4/1978  Berazosky et al. ............ 564/215
4,086,274  4/1978  Kaiser et al. ................. 564/215
4,279,819  7/1981  Price et al. ................... 549/494

OTHER PUBLICATIONS

Frump, Chemical Reviews, vol. 71, (1971), No. 5, pp. 483–505.
Wiley et al, Chemical Reviews, vol. 44, (1949), pp. 447–476.
Wehrmeister, J. Org. Chem., vol. 28, (1963), pp. 2587–2588, 2589–2591.

*Primary Examiner*—Richard L. Raymond
*Attorney, Agent, or Firm*—Charles J. Enright

[57] ABSTRACT

A process for making N-furfurylthioalkyl carboxamide by reacting an oxaz(ol)ine with furfurylmercaptan in the absence of a transition metal catalyst. The carboxamide may then be hydrolyzed to form the 2-furfurylthioalkylamine.

13 Claims, No Drawings

PROCESSES FOR MAKING THIOALKYL CARBOXAMIDES AND AMINES

FIELD OF THE INVENTION

The invention comprises a process for making N-furfurylthioalkyl carboxamides.

BACKGROUND OF THE INVENTION

The title compounds are useful as intermediates in making polymeric peptizers as described in U.S. Pat. No. 3,615,624 (Table II) and as intermediates in making pharmaceuticals such as Ranitidine and others as described in U.S. Pat. Nos. 4,128,658, 4,169,855, 4,255,440 and 4,279,819. All of these patents are hereby incorporated by reference.

This class of compounds may be made by the method of U.S. Pat. No. 3,615,624 which reacts ethyleneimine with 2-furylmethylthiol (Table 2, No. 4), however, ethyleneimine is highly toxic, and difficult to work with commercially.

This class of compounds may also be made by reacting furfurylmercaptan with bromoethyl phthalimide and then removing the phthalic acid moiety by reaction, for example, with hydrazine hydrate as taught in U.S. Pat. No. 4,279,819 (Column 7). However, this requires two-steps with purifications and expensive reagents which are lost as by-products.

U.S. Pat. No. 4,086,273, which is hereby incorporated by reference, discloses a reaction of an aliphatic mercaptan with a 2-oxazoline in the presence of a transition metal catalyst. This patent teaches that the aliphatic mercaptans do not give good yields of the adduct without use of the catalyst. If the product is to be used as a pharmaceutical, it should be carefully purified of metal residue. Any residue may have an adverse effect on further reactions or may ultimately show up in the product which is undesirable if the metal is at all toxic.

OBJECTS OF THE INVENTION

It is an object of the invention to provide a process for making N-furfurylthioalkyl carboxamides. It is a preferred object of the invention to make this compound without the use of ethyleneimine or transition metal catalysts and without the use of expensive reagents, which do not end up in the final product.

SUMMARY OF THE INVENTION

One or more of these and/or other objects of the invention may be met by a process for making N-furfurylthioalkyl carboxamide by reacting an oxaz(ol)ine with furfurylmercaptan in the absence of a transition metal catalyst. The carboxamide may then be hydrolyzed to yield an amine.

DETAILED DESCRIPTION

The furfurylmercaptan starting materials are known compounds represented by the formula I:

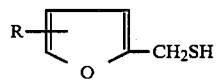

The R group may be hydrogen, alkyl, alkenyl, cycloalkyl, aryl, aralkyl, alkylaryl, or one of these substituted with or interrupted by an oxygen, nitrogen or halogen atom. Preferably R has less than 25 carbon atoms. The one proviso is that R does not react with the oxazoline to an appreciable extent. One class of the R substituent is described in U.S. Pat. No. 4,279,819 (Column 1) by the formula Ia:

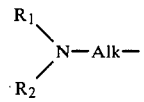

wherein $R_1$ and $R_2$ which may be the same or different represent hydrogen, lower alkyl, cycloalkyl, lower alkenyl, aralkyl, or lower alkyl interrupted by an oxygen atom or a group

in which $R_4$ represents hydrogen or lower alkyl, or $R_1$ and $R_2$ may together with the nitrogen atom to which they are attached, form a heterocyclic ring which may contain other hetero atoms selected from O and

Alk denotes a straight or branched alkylene chain of 1-6 carbon atoms. Preferably, R is hydrogen or the substituent Ia from the aforementioned patent. Also preferably R is attached to the carbon atom adjacent the oxygen atom that is not attached to the thiol group. Of the substituents from the aforementioned patent, it is most preferred that $R_1$ and $R_2$ be methyl and the Alk group be methylene.

These mercaptans are available commercially. The substituted mercaptans wherein R is not hydrogen may be synthesized from the unsubstituted mercaptan by, for example, a Mannich reaction with a dialkylamine hydrochloride.

The oxaz(ol)ine, which encompasses both oxazolines and oxazines starting materials II:

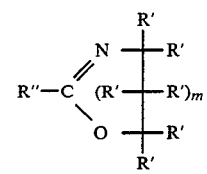

are also known materials and are described, for example, in Frump Chemical Reviews, 1971, Vol. 71, No. 5, page 483-505; Wiley et al., Chemical Reviews, Vol. 44, pages 447-476, 1949; and Seeliger, Angew. Chem. Internat. Edit., Vol. 5, No. 10, (1966) pages 875-888. These three references are hereby incorporated by reference.

The substituents R' and R" may be hydrogen, alkyl, aryl, alkenyl, cycloalkyl, alkylaryl, and aralkyl or one of these substituted or interrupted with an oxygen, nitrogen or halo atom and m is 0 or 1. Each R' and R" which each preferably contain less than 25 carbon atoms may be one or more of the substituents independently. R' and R" are preferably $C_1$-$C_8$ alkyl or hydrogen. R' is most preferably hydrogen. R" is more preferably an inexpensive leaving group such as methyl or ethyl since it does not end up in the product and m is preferably zero. When m is zero, II is an oxazoline. When m is one, II is an oxazine.

The N-furfurylthioalkylcarboxamide formed by the process of the invention is shown by the formula III:

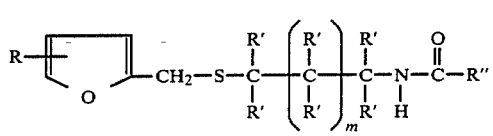

wherein R, R', R" and m have the aforementioned definitions. The formula III is meant to cover tautomers stereoisomers and optical enantiomers inherent in the above definitions of the product.

The carboxamide III is prepared by contacting the oxaz(ol)ine II and the furfurylmercaptan I in the absence of a transition metal catalyst. Generally, the oxaz-(ol)ine is added to the furfurylmercaptan.

The pressure under which the reaction is conducted may vary from less than atmospheric to superatmospheric pressures. A pressure range from 1 atm to 2 atm is preferred. Atmospheric pressure is most preferred.

The reaction may be run at any temperature at which appreciable product III is formed. The reaction occurs at temperatures from 100° C. to 250° C. More preferably the temperature range of the reaction varies from 125° C. to 200° C. And most preferably, from 150° C. to 190° C.

The reaction works efficiently in the absence of a transition metal catalyst taught by the art. Preferably no catalyst or accelerator at all is used in the process.

The product may then be isolated from the reaction mixture by distillation at reduced pressure. Yields without a catalyst may be greater than 20 mole percent based on either reactant. Yields are preferably greater than 50 percent, most preferably greater than 80 percent and under ideal conditions may approach 95 mole percent or greater.

The N-furfurylthioalkyl carboxamide III may be converted to the furfurylthioalkylamine IV

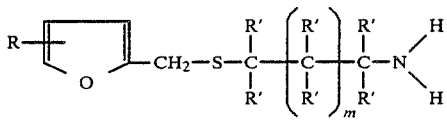

by hydrolysis with either acid or base in water. Base is preferred. R, R' and m have their aforementioned meanings. Exemplary bases include the alkali metal hydroxides. Elevated temperatures and pressures may be used in order to hasten the hydrolysis. The furfurylthioalkylamine may be extracted with an organic solvent such as chloroform, dried and then separated by distillation or stripping.

EXAMPLE 1

In this example furfurylmercaptan and 2-ethyl-2-oxazoline are reacted to form N-furfurylthioethylpropionamide. Furfurylmercaptan (13.04 grams, 0.11 mols) is heated under nitrogen to 155° C. in a flask. 2-Ethyl-2-oxazoline (11.4 grams, 0.115 mols) is slowly added from a dropping funnel over a period of two hours. The mixture is post-reacted at 155° C. for an additional 1½ hours. The product is isolated by distillation at reduced pressure: BP 136°–137° C. at 0.2 millimeters Hg. The spectral and elemental analyses correspond to those of the N-furfurylthioethylpropionamide mentioned above. Analysis for the crude reaction mixture by internal standard gas/liquid chromatography shows 1.7 weight percent 2-ethyl-2-oxazoline, 0.8 weight percent furfurylmercaptan and 95.8 weight percent N-(2-furfurylthioethyl)propionamide. This is a reaction yield based on starting materials of 96 percent.

EXAMPLE 2

Formation of the 2-furfurylthioethylamine. The propionamide of Example 1 (4.8 grams, 22.5 mmol) and 10 grams of 10 percent sodium hydroxide are charged into a stainless steel Parr reactor and heated to 135° C. After 24 hours the reactor is cooled and the hydrolysis product is extracted with 50 ml of chloroform. The extract is dried over magnesium sulfate and the solvent is stripped on a rotary evaporator at reduced pressure. The spectral data and elementary analysis of the resulting product is consistent with 2-furfurylthioethylamine.

In order to obtain the 2-furfurylthioethylamines listed in U.S. Pat. No. 4,279,819, one may contact the product of Example 2 with formaldehyde and a dialkyl amine hydrochloride in a Mannich reaction.

Although the invention has been described in considerable detail, it must be understood that such detail is for the purpose of illustration only and that many variations and modifications can be made by one skilled in the art without departing from the spirit and scope of the invention.

We claim:
1. A process for making N-furfurylthioalkyl carboxamide by reacting an oxaz(ol)ine with a furfurylmercaptan in the absence of a transition metal catalyst to yield greater than 50 mole percent N-furfurylthioalkyl carboxamide based on either reactant.
2. The process of claim 1 wherein the furfurylmercaptan is of the formula

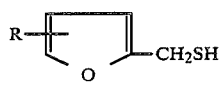

wherein R is hydrogen, alkyl, alkenyl, aryl, aralkyl, alkylaryl, or one of these substituted with or interrupted by an oxygen, nitrogen or halogen atom.
3. The process of claim 2 wherein R is attached to the carbon atom adjacent the oxygen atom.
4. The process of claim 3 wherein R is

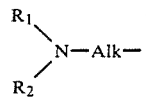

wherein $R_1$ and $R_2$ which may be the same or different represent hydrogen, lower alkyl, cycloalkyl, lower alkenyl, aralkyl, or lower alkyl interrupted by an oxygen atom or a group

in which R₄ represents hydrogen or a lower alkyl, or R₁ and R₂ may together with the nitrogen atom to which they are attached form a heterocyclic ring which may contain other hetero atoms selected from O and

and Alk denotes a straight or branched chain of 1–6 carbon atoms.

5. The process of claim 4 wherein R₁ and R₂ are methyl or ethyl and Alk is a methylene group.

6. The process of claim 3 wherein the oxaz(ol)ine is of the formula

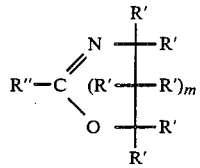

wherein each R' and R" is independently hydrogen, alkyl aryl, alkenyl, alkylaryl, aralkyl, cycloalkyl, or one of these substituted or interrupted with an oxygen, nitrogen or halogen atom and m is 0 or 1.

7. The process of claim 6 wherein m is zero and each R' is hydrogen.

8. The process of claim 7 wherein R" is methyl or ethyl.

9. The process of claim 1 wherein the N-furfurylthioalkyl carboxamide is formed at a greater than 80 mole percent yield based on either reactant.

10. A process to form a furfurylthioalkylamine of the formula:

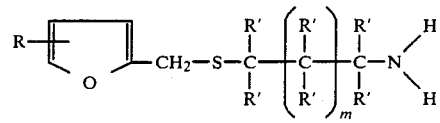

by contacting a furfurylmercaptan of the formula:

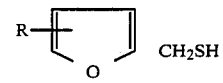

with an oxaz(ol)ine of the formula:

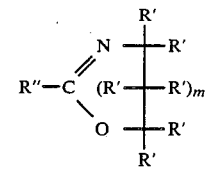

wherein R, R' and R" are each independently hydrogen, alkyl, alkenyl, aryl, aralkyl, alkylaryl, or one of these substituted with or interrupted by an oxygen, nitrogen or halogen atom, and m is zero or one, to form a N-furfurylthioalkyl carboxamide in the absence of a transition metal catalyst at a yield of greater than 50 mole percent N-furfurylthioalkyl carboxamide based on either reactant and then hydrolyzing the carboxamide to the amine.

11. The process of claim 10 wherein R is attached to the carbon atom adjacent the oxygen atom.

12. The process of claim 11 wherein R and each R' is hydrogen, R" is methyl or ethyl and m is zero.

13. The process of claim 10 wherein the hydrolysis step is carried out in the presence of aqueous base.

* * * * *